(12) United States Patent
Tada et al.

(10) Patent No.: US 12,226,118 B2
(45) Date of Patent: Feb. 18, 2025

(54) MEDICAL DEVICE

(71) Applicant: TERUMO KABUSHIKI KAISHA, Tokyo (JP)

(72) Inventors: Yuichi Tada, Santa Clara, CA (US); John Barritt, San Jose, CA (US)

(73) Assignee: TERUMO KABUSHIKI KAISHA, Tokyo (JP)

( * ) Notice: Subject to any disclaimer, the term of this patent is extended or adjusted under 35 U.S.C. 154(b) by 387 days.

(21) Appl. No.: 17/868,715

(22) Filed: Jul. 19, 2022

(65) Prior Publication Data
US 2022/0354530 A1    Nov. 10, 2022

Related U.S. Application Data

(63) Continuation of application No. PCT/JP2020/004567, filed on Feb. 6, 2020.

(51) Int. Cl.
*A61B 17/3207* (2006.01)
*A61B 17/32* (2006.01)

(52) U.S. Cl.
CPC .............. *A61B 17/320758* (2013.01); *A61B 2017/320052* (2013.01)

(58) Field of Classification Search
CPC ........... A61B 17/320758; A61B 2017/320052; A61B 2017/320791; A61B 2090/08021; A61B 2217/005; A61B 17/320783; A61B 2017/320766
See application file for complete search history.

(56) References Cited

U.S. PATENT DOCUMENTS

| | | | |
|---|---|---|---|
| 9,788,854 B2 | 10/2017 | Simpson et al. |
| 2007/0088230 A1 | 4/2007 | Terashi et al. |
| 2012/0016344 A1 | 1/2012 | Kusakabe |
| 2014/0005699 A1 | 1/2014 | Bonnette et al. |
| 2017/0319805 A1 | 11/2017 | Herdina et al. |
| 2018/0218807 A1 | 8/2018 | Takahashi |

(Continued)

FOREIGN PATENT DOCUMENTS

| | | |
|---|---|---|
| JP | 2007-068970 A | 3/2007 |
| JP | 2012-035059 A | 2/2012 |
| JP | 2015-521903 A | 8/2015 |

(Continued)

OTHER PUBLICATIONS

English Translation of International Search Report dated Mar. 24, 2020, mailed in counterpart International Application No. PCT/JP2020/004567, 2 pages.

(Continued)

*Primary Examiner* — Richard G Louis
(74) *Attorney, Agent, or Firm* — Kim & Stewart LLP

(57) ABSTRACT

A medical device that removes an object in a body lumen, includes a rotatable drive shaft, a cutter attached to a distal portion of the drive shaft and by which the object is cut, an outer tube surrounding the drive shaft, a guide wire tube attached to a distal portion of the outer tube and having a guide wire lumen therein, a metal member attached to the guide wire tube and including a first portion that extends along the guide wire tube and includes a first recess, and a distal tip made of a resin, disposed at a distal portion of the guide wire tube, and having a distal lumen that communicates with the guide wire lumen. The distal tip engages with the first recess of the metal member.

20 Claims, 6 Drawing Sheets

(56) References Cited

U.S. PATENT DOCUMENTS

2018/0353199 A1    12/2018    Tada et al.

FOREIGN PATENT DOCUMENTS

| JP | 2018-125935 A | 8/2018 |
| JP | 2019-058198 A | 4/2019 |

OTHER PUBLICATIONS

English Translation of Written Opinion dated Mar. 24, 2020, mailed in counterpart International Application No. PCT/JP2020/004567, 3 pages.
Notice of Reasons for Refusal mailed Jun. 12, 2023 in corresponding Japanese Patent Application No. 2021-575187, 11 pages (with Translation).

MEDICAL DEVICE

CROSS-REFERENCE TO RELATED APPLICATION(S)

This application is a continuation of International Patent Application No. PCT/JP2020/004567 filed Feb. 6, 2020, the entire contents of which are incorporated herein by reference.

BACKGROUND OF THE INVENTION

Field of the Invention

This disclosure relates to a medical device for removing an object in a body lumen such as a blood vessel, a medical system including a medical device, and a method of removing an object in a body lumen using a medical device.

Background Art

Examples of treatment methods for a stenosed site caused by a plaque, a thrombus, and the like in a blood vessel include a method for dilating the blood vessel using a balloon, and a method for causing a mesh-shaped or coil-shaped stent to indwell the blood vessel as a support for the blood vessel. However, it is difficult for these methods to treat a stenosed site that is hardened by calcification or a stenosed site that is formed at a bifurcated portion in the blood vessel. A method to treat such a stenosed site includes cutting and removing the stenotic material such as a plaque or a thrombus.

For example, a conventional device includes a cutting portion that cuts an object in a blood vessel by rotating. Such a device is a rapid exchange type device in which a guide wire lumen is disposed only at a distal portion thereof. The distal portion of the device is made of a metal material.

When the distal portion of the device is made of the metal material, the distal portion has high rigidity and is difficult to bend. Therefore, followability to a guide wire is reduced, and it is difficult to follow the complicated blood vessel. In addition, when a resin member is connected to the metal member, the resin member is easily detached from the metal member.

SUMMARY OF THE INVENTION

A medical device according to this disclosure that achieves the above object is a medical device that removes an object in a body lumen. The medical device includes: a rotatable drive shaft, a cutter attached to a distal portion of the drive shaft and by which the object is cut, an outer tube surrounding the drive shaft, a guide wire tube attached to a distal portion of the outer tube and having a guide wire lumen therein, a metal member attached to the guide wire tube and including a first portion that extends along the guide wire tube and includes a first recess, and a distal tip made of a resin, disposed at a distal portion of the guide wire tube, and having a distal lumen that communicates with the guide wire lumen. The distal tip engages with the first recess of the metal member.

In the medical device configured as described above, the distal tip disposed on the distal side with respect to the metal member and made of the resin is more flexibly deformed than the metal member. Therefore, in the medical device, followability to a guide wire to be inserted into the guide wire lumen and the body lumen is improved. Further, since the distal tip is inserted into the recess, peeling and separation from the metal member is prevented. Therefore, the medical device includes the metal member on the distal side with respect to the cutting portion, has high followability to the guide wire and the body lumen, and can prevent breakage of the distal tip made of the resin.

DESCRIPTION OF EMBODIMENTS

Figure 1:
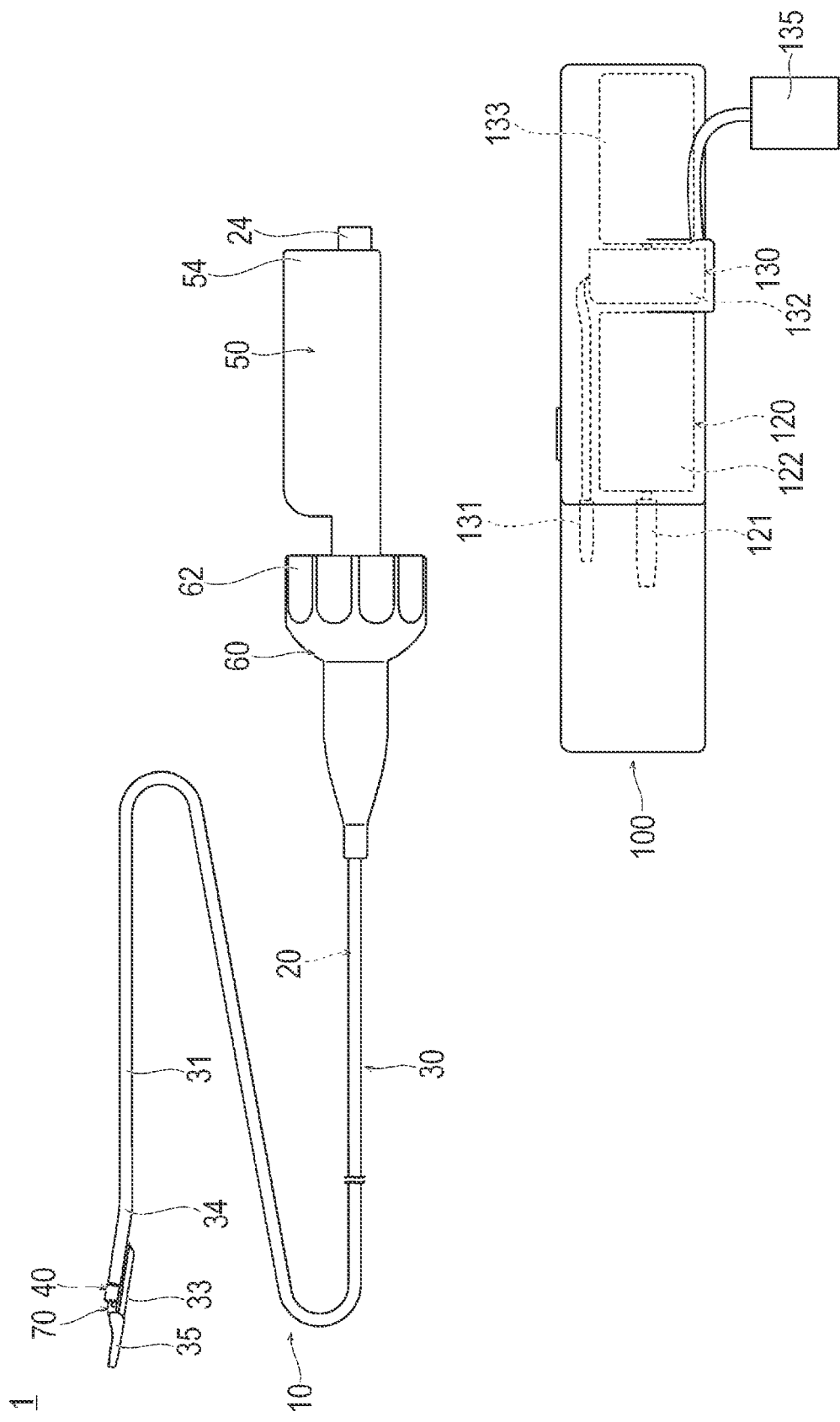
FIG. 1 is a front view of a medical device and a drive device according to an embodiment.

Hereinafter, embodiments according to the disclosure will be described with reference to the drawings. Note that a size and a ratio of each member in the drawings may be exaggerated for convenience of description and may differ from its actual size and ratio.

A medical device 10 according to an embodiment is inserted into a blood vessel in an acute lower limb ischemia or a deep vein thrombosis, and is used for destroying and removing a thrombus, a plaque, an atheroma, a calcified lesion, or the like. In the present specification, a side (or portion) of the device to be inserted into a blood vessel is referred to as a "distal side (or portion)", and a side (or portion) to be operated by an operator is referred to as a "proximal side (or portion)". Note that an object to be removed by the medical device 10 is not necessarily a thrombus, a plaque, an atheroma, or a calcified lesion, and any object that may be present in a body lumen can be removed by the medical device 10.

As shown in FIG. 1, the medical device 10 is interlocked with and driven by a drive device 100 that generates a driving force. The medical device 10 and the drive device 100 make up one medical system 1.

As shown in FIGS. 1 to 4, the medical device 10 includes a long drive shaft 20 that is rotationally driven, an outer tube 30 that accommodates the drive shaft 20, a cutting portion 40 that cuts an object such as a thrombus, and a guide wire tube 33 into which a guide wire W (see FIG. 3B) can be inserted. The medical device 10 further includes a distal tip 35 that is interlocked with a distal portion of the guide wire tube 33, a metal member 70 that is interlocked with a distal portion of the outer tube 30, a first fixing tube 90 that fixes the guide wire tube 33 to the metal member 70, and a second fixing tube 91 that fixes the guide wire tube 33 to the outer tube 30. The medical device 10 further includes a first housing 50 that rotatably holds a proximal portion of the drive shaft 20, and a second housing 60 that is interlocked with a proximal portion of the outer tube 30.

Figure 2:
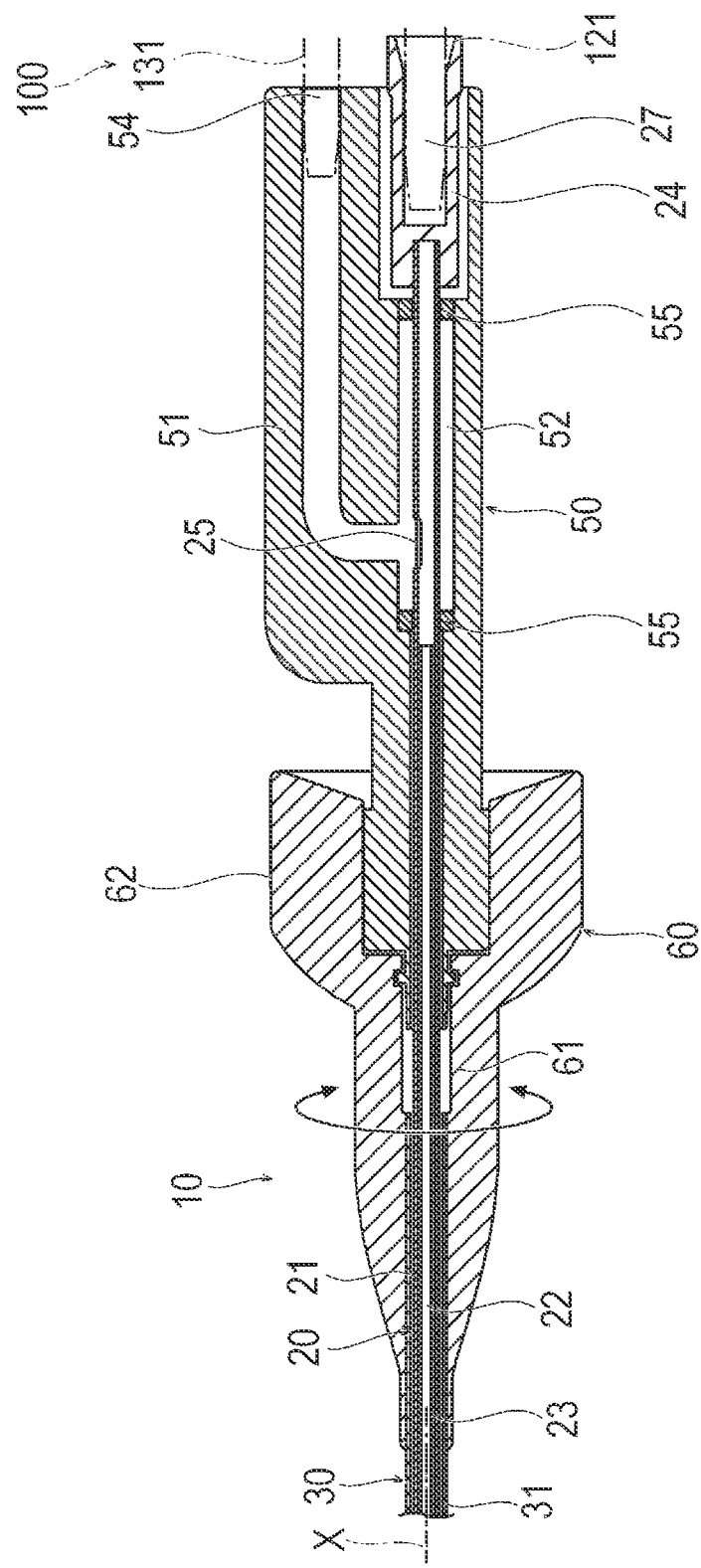
FIG. 2 is a cross-sectional view of a proximal portion of a medical device according to an embodiment.
Figure 3A:
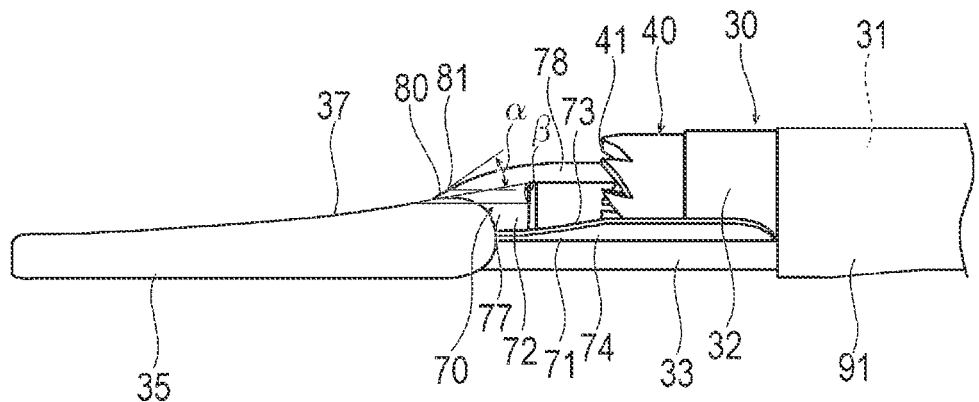
FIGS. 3A and 3B show diagrams of a distal portion of a medical device according to an embodiment.
Figure 3B:
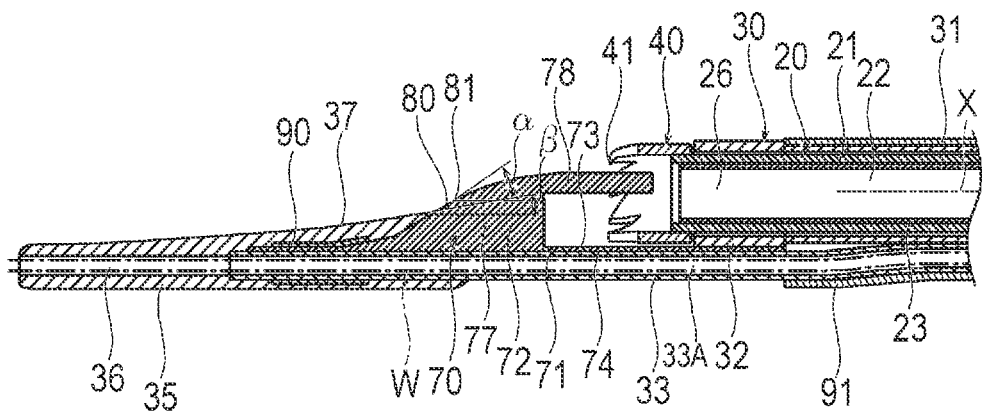
Figure 4A:
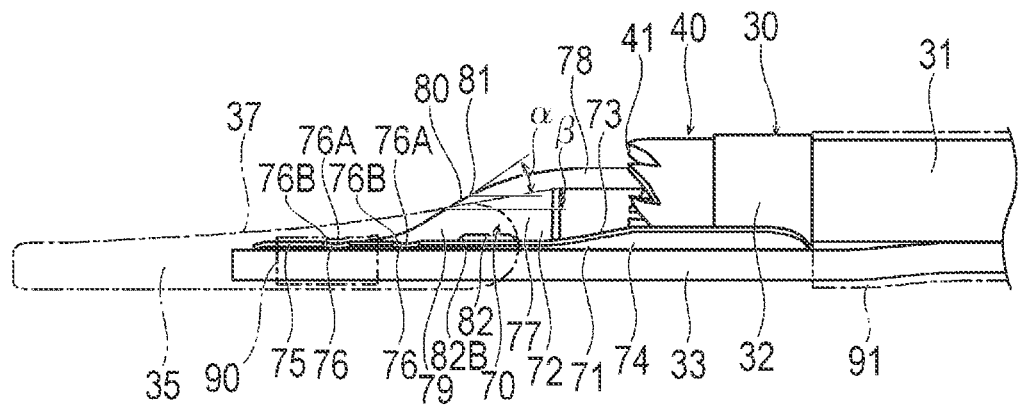
FIGS. 4A and 4B show diagrams of a distal portion of a medical device according to an embodiment.
Figure 4B:
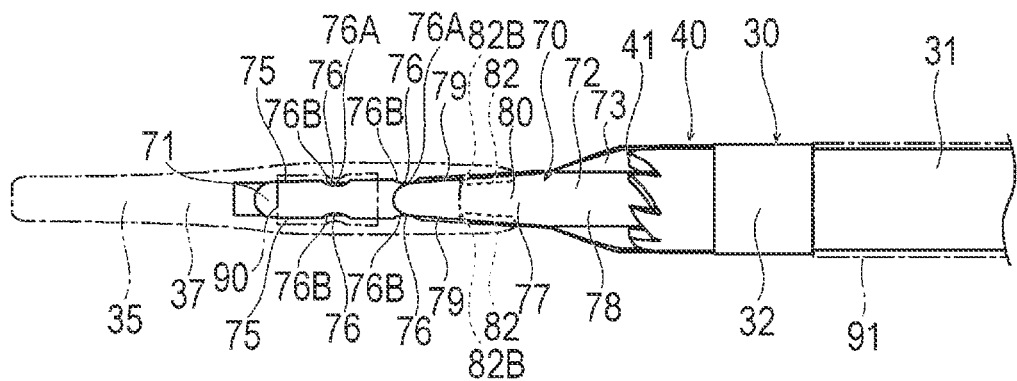

As shown in FIG. 2 and FIG. 3B, the drive shaft 20 transmits a rotational force to the cutting portion 40. The drive shaft 20 is formed with an aspiration lumen 22 for transporting a cut object to the proximal side. The drive shaft 20 extends along an axis X and includes a long tubular drive tube 21, an inner tube 23 disposed inside the drive tube 21, and a rotary input portion 24 fixed to a proximal portion of the drive tube 21.

The drive tube 21 penetrates the outer tube 30, and the cutting portion 40 is fixed to a distal portion thereof. The proximal portion of the drive tube 21 is located inside the second housing 60. The drive tube 21 is rotationally driven by a rotary drive shaft 121, which will be described later, via the rotary input portion 24. The drive tube 21 includes, at a distal end thereof, an inlet portion 26 into which debris, which is an object to be aspirated such as a cut thrombus, enters. The lumen of a proximal end of the drive tube 21 is closed, and the proximal end of the drive tube 21 is fixed to the rotary input portion 24. The drive tube 21 includes, at a proximal portion located inside the second housing 60, a lead-out portion 25 through which the aspiration lumen 22 opens laterally. The lead-out portion 25 is an outlet from which the debris that entered an inside of the drive tube 21 from the inlet portion 26 is discharged.

The drive tube 21 is flexible and transmits rotational power from the proximal side to the distal side. The drive tube 21 may be formed of one member as a whole, or may be formed of a plurality of members. The drive tube 21 may have a spiral slit or groove formed by laser processing or the like in order to adjust rigidity depending on its portions. In addition, the distal portion and the proximal portion of the drive tube 21 may be made of different members. The inner tube 23 is a tubular body having flexibility, and is disposed inside the drive shaft 20. The inner tube 23 is disposed inside the drive tube 21. The inner tube 23 prevents an inner peripheral surface of the drive tube 21 from being damaged due to the debris flowing inside the drive tube 21.

In one embodiment, the inner tube 23 may be omitted from the drive tube 21.

As a constituent material for the drive tube 21, for example, stainless steel, Ta, Ti, Pt, Au, W, polyolefins such as polyethylene and polypropylene, polyamides, polyesters such as polyethylene terephthalate, fluoropolymers such as an ethylene tetrafluoroethylene copolymer (ETFE), polyether ether ketone (PEEK), and polyimides can be preferably used. In addition, the drive tube 21 may be made of a plurality of materials, and a reinforcing member such as a wire rod may be embedded therein.

As shown in FIG. 2, the rotary input portion 24 is a substantially cylindrical member fixed to the proximal end of the drive tube 21. The rotary input portion 24 is interlocked with the rotary drive shaft 121 of the drive device 100 to receive the rotational power. A proximal portion of the rotary input portion 24 includes a fitting recess 27 into which the rotary drive shaft 121 is fitted.

As shown in FIGS. 2 to 4B, the outer tube 30 includes an outer tube main body 31 that rotatably accommodates the drive shaft 20, and an outer tube distal portion 32 that is disposed at a distal portion of the outer tube main body 31.

The outer tube main body 31 is a tubular body, and a proximal portion thereof is fixed to the second housing 60. The distal portion of the outer tube main body 31 is located on a proximal side of the outer tube distal portion 32. The outer tube main body 31 includes, at the distal portion, a curved portion 34 that bends at a predetermined angle. The curved portion 34 can be used for changing a direction of a distal end of the outer tube main body 31 by rotating the outer tube main body 31.

A constituent material for the outer tube main body 31 is not particularly limited, and for example, polyolefins such as polyethylene and polypropylene, polyamides, polyesters such as polyethylene terephthalate, various elastomers, fluoropolymers such as ETFE, PEEK, and polyimides can be preferably used. In addition, the outer tube main body 31 may be made of a plurality of materials, and a reinforcing member such as a wire rod may be embedded therein.

The cutting portion 40 is a cutter that cuts and reduces an object such as a thrombus, a plaque, or a calcified lesion. Therefore, the "cut" means applying a force to the object in contact to make the object smaller. A method for applying the force in the cutting and a shape or a form of the object after the cutting are not limited. The cutting portion 40 has strength to cut the above-described object. The cutting portion 40 is fixed to the distal portion of the drive tube 21. The cutting portion 40 has a tubular shape and protrudes toward the distal side with respect to the drive tube 21. A distal end of the cutting portion 40 is provided with a sharp blade 41. Note that a shape of the blade 41 is not particularly limited. The cutting portion 40 may have a large number of minute abrasive grains instead of the blade 41.

A constituent material for the cutting portion 40 preferably has sufficient strength to cut a thrombus, and for example, stainless steel, Ta, Ti, Pt, Au, W, and a shape memory alloy can be preferably used. The constituent material for the cutting portion 40 may be a resin such as engineering plastics such as polyether ether ketone (PEEK).

The outer tube distal portion 32 has a tubular shape and is fixed to the distal portion of the outer tube main body 31. The outer tube distal portion 32 is disposed on a proximal side of the cutting portion 40 and is slidable with respect to the cutting portion 40. The metal member 70 is interlocked with an outer peripheral surface of the outer tube distal portion 32. As a constituent material for the outer tube distal portion 32, for example, stainless steel, Ta, Ti, Pt, Au, W, polyolefins such as polyethylene and polypropylene, polyamides, polyesters such as polyethylene terephthalate, fluoropolymers such as an ethylene tetrafluoroethylene copolymer (ETFE), polyether ether ketone (PEEK), and polyimides can be preferably used.

As shown in FIGS. 1, 3A, 3B, 4A, and 4B, the guide wire tube 33 is formed with a guide wire lumen 33A into which the guide wire W can be inserted. A proximal portion of the guide wire tube 33 is fixed to an outer peripheral surface of the distal portion of the outer tube main body 31. The distal portion of the guide wire tube 33 is fixed to the metal member 70 and the distal tip 35 on the distal side with respect to the cutting portion 40. The medical device 10 is a rapid exchange type device in which the guide wire lumen 33A is formed only at a distal portion thereof. The constituent material for the guide wire tube 33 is not particularly limited, but preferably has a melting point higher than a melting point of the distal tip 35, and for example, polyimides, polyether ether ketone (PEEK), or the like can be preferably used. Note that the constituent material for the guide wire tube 33 is not limited thereto, and may be, for example, polyolefins such as polyethylene and polypropylene, polyamides, polyesters such as polyethylene terephthalate, various elastomers, and fluoropolymers such as an ethylene tetrafluoroethylene copolymer (ETFE).

Figure 6A:
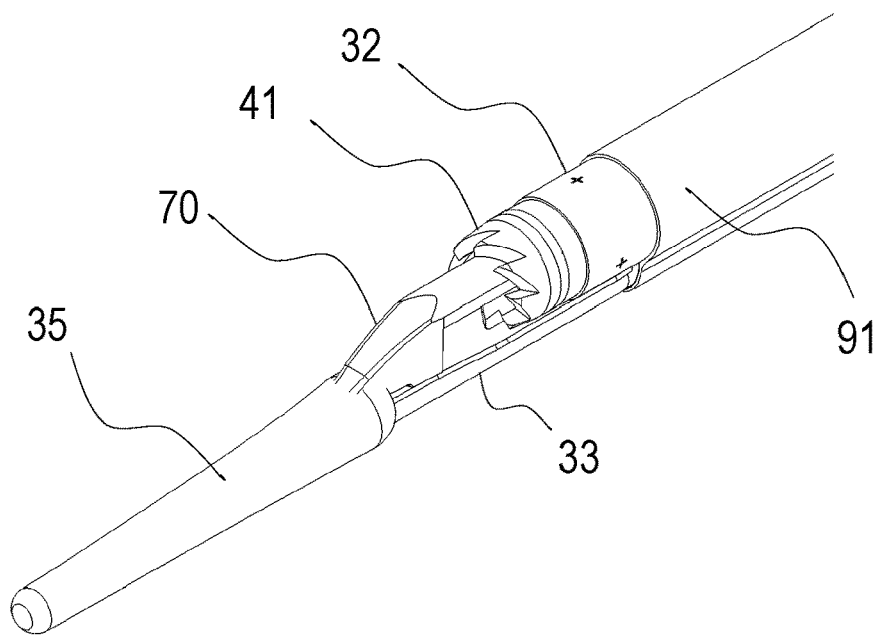
FIGS. 6A and 6B show diagrams of a distal portion of a medical device according to an embodiment.
Figure 6B:
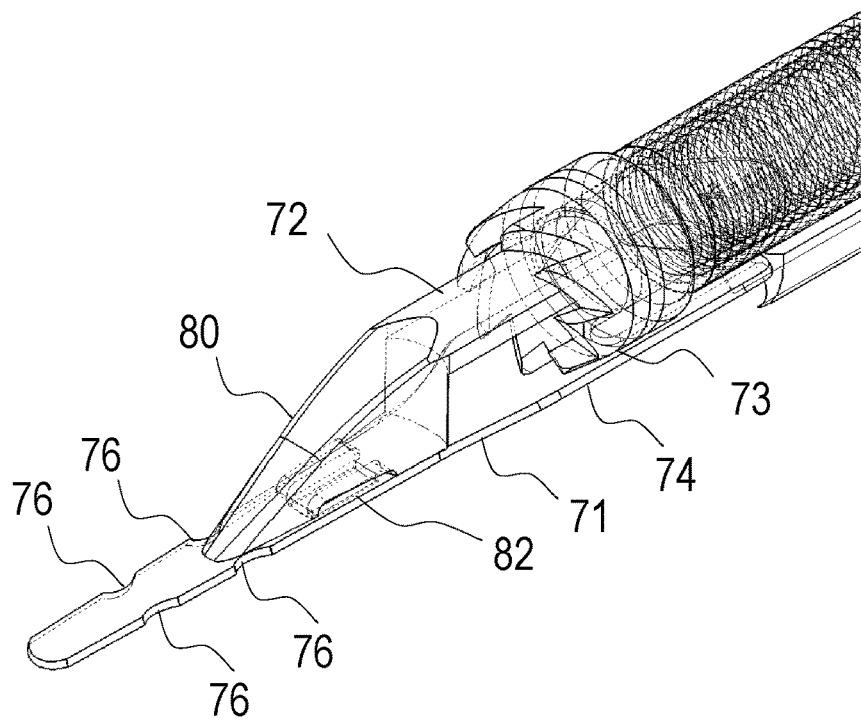

The metal member 70 includes a fixing portion 71 that is interlocked with the outer tube distal portion 32 and extends toward the distal side with respect to the cutting portion 40, and a stopper 72 that is interlocked with the fixing portion 71. The detail of the metal member 70 is shown in FIGS. 6A and 6B. The fixing portion 71 has a substantially plate shape, and includes a first surface 73 and a second surface 74 extending along the axis X of the drive shaft 20. The first surface 73 and the second surface 74 are surfaces of the fixing portion 71 having the substantially plate shape. The first surface 73 faces the outer tube 30 and the cutting portion 40. The second surface 74 faces the opposite side of the first surface 73 and is in contact with the guide wire tube 33. A proximal portion of the first surface 73 is fixed to the outer peripheral surface of the outer tube distal portion 32. The proximal portion of the first surface 73 is curved along the outer peripheral surface of the outer tube distal portion 32. A distal portion of the first surface 73 is fixed to the stopper 72.

The fixing portion 71 has first recesses 76 on two side surfaces 75 between the first surface 73 and the second surface 74. The first recesses 76 are formed in a cutout or groove shape so as to extend from the first surface 73 of the fixing portion 71 to the second surface 74. Each first recess 76 has a recessed shape having a bottom 76A corresponding to the deepest portion of the first recess 76 and recessed with respect to the distal side and the proximal side. At least a part of an inner surface 76B of the first recess 76 faces the proximal side. The inner surface 76B is a recessed surface of the first recess 76. The inner surface 76B may be a flat surface or a surface (for example, a curved surface) other than the flat surface. Note that a normal direction of the inner surface 76B of the first recess 76 facing the proximal side may or may not be parallel to the axis X as long as the normal direction has a proximal direction component. When a force in the direction along the axis X is applied between the distal tip 35 and the metal member 70, because of the material of the distal tip 35 fixed to the first recess 76 therein, the distal tip 35 is difficult to move with respect to the first recess 76. In particular, since at least a part of the inner surface 76B of the first recess 76 faces the proximal side, the material of the distal tip 35 in the first recess 76 is fixed to the inner surface 76B of the first recess 76, and is difficult to come off from the first recess 76. Therefore, a coupling force between the distal tip 35 and the metal member 70 in the direction along the axis X is improved. Since a plurality of (two in the present embodiment) first recesses 76 are provided on each side surface 75, the coupling force between the distal tip 35 and the metal member 70 is improved.

When the stopper 72 is in contact with a wall of the body lumen, the stopper 72 can stop movement of the cutting portion 40 toward the wall in a radial direction of the body lumen. The stopper 72 is fixed to a portion of the first surface 73 on the distal side with respect to the cutting portion 40. The stopper 72 includes a stopper distal portion 77 fixed to the first surface 73 and a stopper proximal portion 78 extending from the stopper distal portion 77 toward the proximal side. The stopper distal portion 77 rises substantially vertically from the first surface 73. The stopper distal portion 77 has two stopper side surfaces 79 facing opposite sides and an inclined portion 80. The two stopper side surfaces 79 are substantially parallel to each other. The two stopper side surfaces 79 face a direction substantially perpendicular to the axis X. The inclined portion 80 is formed on a side of the stopper distal portion 77 opposite to a side fixed to the fixing portion 71. The inclined portion 80 is inclined such that a distance from the fixing portion 71 increases toward the proximal side. An inclination angle α of the inclined portion 80 with respect to the first surface 73 (or the axis X) is, for example, 10° to 80° at a portion 81 where the inclination angle α of the inclined portion 80 is the largest. When the stopper distal portion 77 is in contact with the wall of the body lumen, the movement of the cutting portion 40 to the wall in the radial direction of the body lumen can be stopped.

The stopper proximal portion 78 is formed so as to be continuous from the inclined portion 80 of the stopper distal portion 77 to the proximal side. The stopper proximal portion 78 is inserted into the cutting portion 40. When the stopper proximal portion 78 is inserted into the cutting portion 40, the stopper proximal portion 78 is in contact with the wall of the body lumen, and stops the movement of the cutting portion 40 toward the wall in the radial direction of the body lumen, thereby preventing cutting of a part of the body lumen that should not be cut. A direction in which the stopper proximal portion 78 extends is parallel to the axis X. The inclination angle α of the inclined portion 80 gradually decreases toward the stopper proximal portion 78. Therefore, a smooth surface is continuously formed between the stopper proximal portion 78 and the inclined portion 80. Therefore, the inclined portion 80 and the stopper proximal portion 78 which are exposed to an outside smoothly come into contact with the body lumen. Therefore, the metal member 70 can be brought into contact with the body lumen by the inclined portion 80 and the stopper proximal portion 78 which are exposed to the outside. Therefore, the metal member 70 can smoothly move in the body lumen and prevent unintended damage to the body lumen.

Second recesses 82 are formed on the stopper side surfaces 79. The second recesses 82 are formed on portions of the stopper side surfaces 79 adjacent to the fixing portion 71. Note that positions at which the second recesses 82 are formed are not limited thereto, and the second recesses 82 may be formed at positions of the stopper side surfaces 79 away from the fixing portion 71. The second recesses 82 are non-through holes having a predetermined depth. Note that the second recesses 82 may be through holes. For example, the second recesses 82 may be formed to penetrate from one stopper side surface 79 to the other stopper side surface 79. The second recesses 82 are disposed on the proximal side with respect to the first recesses 76. Since the second recesses 82 are non-through holes or through holes, the second recesses 82 have a recessed shape recessed with respect to the distal side and the proximal side. At least a part of inner surfaces 82B of the second recesses 82 faces the proximal side. The inner surface 82B is a recessed surface of the second recess 82. The inner surface 82B may be a flat surface or a surface (for example, a curved surface) other than the flat surface. Note that a normal direction of the inner surface 82B of the second recess 82 facing the proximal side may or may not be parallel to the axis X as long as the normal direction has a proximal direction component. Therefore, when a force in the direction along the axis X is applied between the distal tip 35 and the metal member 70, because of the material of the distal tip 35 fixed to the second recess 82 therein, the distal tip 35 is difficult to move with respect to the second recess 82. In particular, since at least a part of the inner surface 82B of the second recess 82 faces the proximal side, the material of the distal tip 35 in the second recess 82 is fixed to the inner surface 82B of the second recess 82, and the distal tip 35 is difficult to move with respect to the second recess 82. Accordingly, the coupling force between the distal tip 35 and the metal member 70 in the direction along the axis X is improved. Since the plurality of second recesses 82 are provided, the coupling force between the distal tip 35 and the metal member 70 is improved. Note that the positions at which the second recesses 82 are disposed are not particularly limited, and for example, the second recesses 82 may be disposed on the distal side with respect to any one of the first recesses 76. In the present specification, the second recesses 82 and the first recesses 76 are collectively referred to as recesses 76 and 82.

The fixing portion 71 and the stopper 72 may be integrally formed, or may be formed by fixing separate members by welding or the like. As a constituent material for the metal member 70, for example, stainless steel, Ta, Ti, Pt, Au, W, polyethylene, or the like can be preferably used.

As shown in FIGS. 3A, 3B, 4A, and 4B, the first fixing tube 90 is a tube for interlocking the metal member 70 with the guide wire tube 33. The first fixing tube 90 can well fix the metal member 70 made of a metal material and the guide wire tube 33 made of a resin material. The first fixing tube 90 surrounds the fixing portion 71 of the metal member 70 and the guide wire tube 33. The first fixing tube 90 is a heat-shrinkable tube. The first fixing tube 90 shrinks at a temperature at which the constituent material (for example, polyimides, PEEK, and the like) of the guide wire tube 33 having high heat resistance softens or at a temperature lower than a melting point. Therefore, even if the first fixing tube 90 is heated to shrink, the guide wire tube 33 is hardly deformed and hardly affected. The first fixing tube 90 surrounds at least one (two in the present embodiment) first recess 76 of the fixing portion 71. The first recess 76 is formed in a cutout or groove shape extending from the first surface 73 of the fixing portion 71 to the second surface 74. Accordingly, the first fixing tube 90 can enter the first recess 76 by being heated and shrinking. Therefore, the first fixing tube 90 can firmly interlock the guide wire W with the metal member 70 having the first recess 76. A constituent material for the heat-shrinkable tube is not particularly limited as long as the material is deformed by heating so that a diameter thereof is shrunk, and for example, polyolefins, fluoropolymers, polyvinyl chloride, and thermoplastic elastomers can be preferably used.

The second fixing tube 91 is a tube for interlocking the outer tube 30 with the guide wire tube 33. The second fixing tube 91 surrounds the outer tube main body 31 and the proximal portion of the guide wire tube 33. The second fixing tube 91 is a heat-shrinkable tube like the first fixing tube 90. The second fixing tube 91 shrinks at the temperature at which the constituent material (for example, polyimides, PEEK, and the like) of the guide wire tube 33 having the high heat resistance softens or at the temperature lower than the melting point. Therefore, even if the second fixing tube 91 is heated to shrink, the guide wire tube 33 is hardly deformed and hardly affected. When the second fixing tube 91 is heated and shrunk, the second fixing tube 91 can firmly interlock the guide wire tube 33 with the outer tube main body 31.

The distal tip 35 covers the distal portion of the guide wire tube 33, a distal portion of the metal member 70, and the first fixing tube 90, and is interlocked with them. The distal tip 35 extends toward the distal side with respect to the guide wire tube 33 and the metal member 70. A distal lumen 36 communicating with the guide wire lumen 33A is formed inside the distal tip 35. The distal lumen 36 extends toward the distal side with respect to the guide wire lumen 33A.

A constituent material for the distal tip 35 is a resin, preferably a thermoplastic resin, and for example, a polymer material such as polyolefins (for example, polyethylene, polypropylene, polybutene, an ethylene-propylene copolymer, an ethylene-vinyl acetate copolymer, an ionomer, or a mixture of two or more kinds thereof), polyvinyl chloride, polyamides, a polyester elastomer, a polyamide elastomer, a polyurethane, a polyurethane elastomer, polyimides, and a fluororesin, or a mixture thereof can be preferably used. Note that in the present specification, the resin includes an elastomer and rubber. The distal tip 35 can be cured and formed after being supplied to surfaces of the guide wire tube 33, the metal member 70, and the first fixing tube 90 in a state of being heated and melted. Note that a method for forming the distal tip 35 is not limited thereto.

Figure 5:
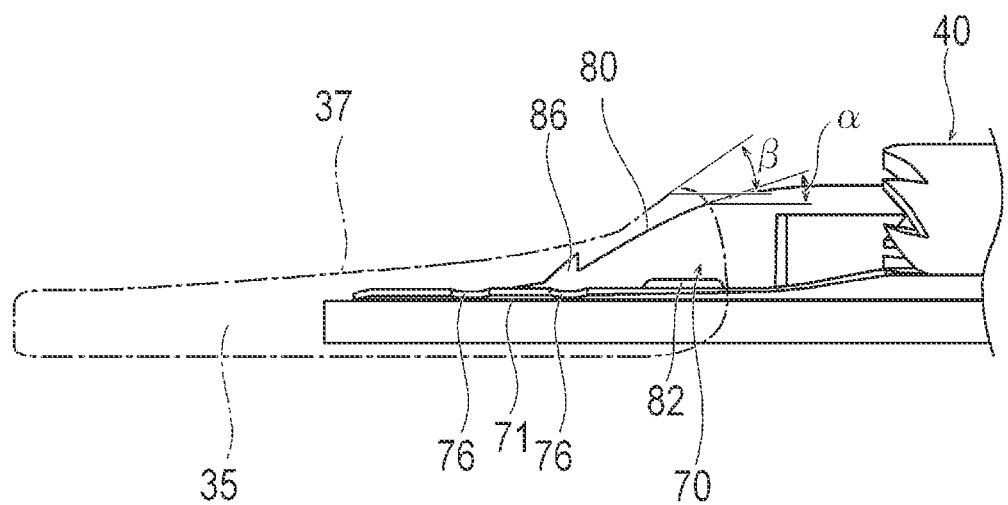
FIG. 5 is a front view of a distal portion of a medical device according to a modification.

The distal tip 35 covers a part of a distal side of the fixing portion 71, a part of a distal side of the inclined portion 80, and a part of distal sides of the stopper side surfaces 79. Accordingly, the distal tip 35 covers the first recesses 76 disposed at the fixing portion 71 and the second recesses 82 disposed at the stopper distal portion 77 while contacting the first recesses 76 and the second recesses 82. The material for the distal tip 35 is fixed to an outer surface of the first fixing tube 90 which is deformed so as to be recessed by being shrunk and entering the first recesses 76. The distal tip 35 includes a tip inclined portion 37 that covers a distal portion of the inclined portion 80. An inclination angle $\beta$ of the tip inclined portion 37 is smaller than the inclination angle $\alpha$ of the most distal side portion (i.e., the portion adjacent to the tip inclined portion 37) of the inclined portion 80 exposed to the outside. Accordingly, a length of the metal member 70 covered with the distal tip 35 in the direction along the axis X can be shortened. Therefore, flexibility of the distal portion of the medical device 10 can be improved. In addition, since the inclined portion 80 of the metal member 70 comes into contact with the body lumen following the tip inclined portion 37, the inclined portion 80 can smoothly come into contact with the body lumen. Note that the inclination angle $\beta$ of the tip inclined portion 37 may be equal to or greater than the inclination angle $\alpha$ of the most distal side portion of the inclined portion 80 exposed to the outside. Accordingly, a length of the metal member 70 covered with the distal tip 35 in the direction along the axis X can be increased. Therefore, it is easy to cover the entire circumference of the metal member 70 with the distal tip 35. Further, since the second recesses 82 of the metal member 70 can be formed to be long in the direction along the axis X, the distal tip 35 is firmly interlocked with the second recesses 82. In addition, as shown in a modification shown in FIG. 5, the inclination angle $\beta$ of the tip inclined portion 37 may be equal to or greater than the inclination angle $\alpha$ of the most distal side portion of the inclined portion 80 exposed to the outside, and an anchor 86 in which the inclination angle $\alpha$ partially increases and that protrudes in a direction away from the fixing portion 71 may be formed in a range of the inclined portion 80 covered with the distal tip 35. Accordingly, the distal tip 35 is fixed not only to the second recesses 82 and the first recesses 76 but also to the anchor 86. Therefore, the distal tip 35 is prevented from peeling off or falling off from the metal member 70.

As shown in FIGS. 1 and 2, the first housing 50 is disposed at a proximal portion of the medical device 10. The first housing 50 is a portion that is interlocked with the drive device 100 and receives a rotational driving force and an aspiration force from the drive device 100. The first housing 50 includes a housing main body 51 that is slidably connected to the second housing 60 in a circumferential direction, an aspiration port 54, and two seal portions 55. An internal space 52 through which the drive tube 21 rotatably penetrates is formed in the housing main body 51. The aspiration port 54 can be connected to an aspiration tube 131 of the drive device 100. The aspiration port 54 communicates with the internal space 52. The proximal portion of the drive tube 21 penetrating the outer tube 30 and the second housing 60 is located in the internal space 52. The lead-out portion 25 of the drive tube 21 is located in the internal space 52. Therefore, a negative pressure applied on the aspiration port 54 from the aspiration tube 131 is then applied on the inside of the drive tube 21 from the lead-out portion 25. The two seal portions 55 prevent the negative pressure in the internal space 52 from escaping.

The second housing 60 is disposed on the distal side of the first housing 50. The second housing 60 is rotatable by fingers of an operator in order to rotate the outer tube 30. The second housing 60 is rotatable relative to the first housing 50, but is not movable relative to the first housing 50 along the axial direction. The second housing 60 includes a passage 61 through which the drive shaft 20 rotatably penetrates, and an operation portion 62 that is operated by the operator to rotate the second housing 60. The proximal portion of the outer tube 30 is interlocked with a distal portion of the passage 61.

Next, the drive device 100 will be described.

As shown in FIG. 1, the drive device 100 includes a drive unit 120 that generates the rotational force and an aspiration unit 130 that generates an aspiration force.

The drive unit 120 includes the rotary drive shaft 121 and a first motor 122 that rotates the rotary drive shaft 121. A rotation speed of the first motor 122 is not particularly limited, and is, for example, 5,000 to 200,000 rpm.

The aspiration unit 130 includes the aspiration tube 131, a pump 132, a second motor 133, and a waste liquid pack 135. The aspiration tube 131 can be connected to the aspiration port 54 of the medical device 10. The pump 132 is driven by the second motor 133 to apply the negative pressure to the aspiration tube 131. In addition, the pump 132 discharges a fluid aspirated through the aspiration tube 131 to the waste liquid pack 135. Note that a configuration of the drive device 100 is not limited to the example described above.

Next, a method of using the medical device 10 according to an embodiment will be described using an example in which a lesion area such as a thrombus or a calcified lesion in a blood vessel is destroyed and aspirated.

First, the operator inserts the guide wire W into a blood vessel and causes the guide wire W to reach the vicinity of a lesion area. Next, the operator inserts the proximal end of the guide wire W into the guide wire lumen 33A of the medical device 10. Thereafter, the medical device 10 is brought to the vicinity of the lesion area by using the guide wire W as a guide. When the medical device 10 is pushed forward in the blood vessel, the medical device 10 is bent so as to follow the guide wire W, and is bent so as to follow the blood vessel that is bent in a complicated manner. The guide wire tube 33 into which the guide wire W is inserted and the distal tip 35 receive a force so as to separate from the metal member 70. In the medical device 10, the distal tip 35 made of a resin is disposed on the metal member 70 disposed on a distal side of the cutting portion 40. That is, the distal tip 35 made of the resin having high flexibility is disposed at a most distal end of the medical device 10 having a metal skeleton (i.e., the metal member 70). Therefore, the medical device 10 can have high pushability and torque transmission performance due to the hard metal member 70 and high followability to the guide wire W and the blood vessel due to the soft distal tip 35. Since the guide wire tube 33 is fixed to the metal member 70 by the first fixing tube 90, peeling off or falling off from the metal member 70 is prevented. Further, since the distal tip 35 engages with the second recesses 82 and the first recesses 76, peeling off or falling off from the metal member 70 is prevented. Therefore, it is possible to achieve the medical device 10 having the high followability to the guide wire W and the blood vessel while having a cutting function by the metal cutting portion 40 and the metal member 70.

When the operator wants to change a position of the cutting portion 40 in a circumferential direction, the operator rotates the operation portion 62 of the second housing 60 while holding the first housing 50. Accordingly, the direction of the curved portion 34 of the outer tube 30 is changed, and the position of the cutting portion 40 can be changed.

Next, the operator connects the medical device 10 to the drive device 100. Accordingly, the rotary drive shaft 121 is connected to the rotary input portion 24. In addition, the aspiration tube 131 is connected to the aspiration port 54. Thereafter, the operator operates the drive device 100. Accordingly, rotation of the rotary drive shaft 121 and aspiration of the aspiration tube 131 are started. The rotary drive shaft 121 rotates the rotary input portion 24. Accordingly, the drive shaft 20 fixed to the rotary input portion 24 and the cutting portion 40 are rotated. The rotating cutting portion 40 cuts the lesion area in the blood vessel.

The aspiration tube 131 applies the negative pressure to the internal space 52 via the aspiration port 54. Therefore, the negative pressure is applied on the aspiration lumen 22 of the drive shaft 20 through the lead-out portion 25 located in the internal space 52. Therefore, as shown in FIG. 3B, the lesion area cut by the blade 41 of the cutting portion 40 becomes debris and moves inside the cutting portion 40 toward the proximal side. The debris is aspirated into the aspiration lumen 22 through the inlet portion 26 of the drive shaft 20.

As shown in FIG. 2, the debris aspirated into the aspiration lumen 22 reaches the pump 132 through the lead-out portion 25, the internal space 52, and the aspiration tube 131. The debris that reached the pump 132 is discharged to the waste liquid pack 135 as shown in FIG. 1. After the cutting of the lesion area and the aspiration of the debris are completed, the operator stops an operation of the drive device 100. Accordingly, the rotation of the drive shaft 20 is stopped, and the aspiration of the pump 132 is stopped. Therefore, the cutting by the cutting portion 40 and the discharge of the debris are stopped. Thereafter, the operator removes the medical device 10 from the blood vessel and completes the procedure.

As described above, the medical device 10 removes an object in a body lumen. The medical device 10 includes: the drive shaft 20 that is rotatable; the cutting portion 40 that is interlocked with a distal portion of the drive shaft 20 and cuts the object; the outer tube 30 that rotatably accommodates the drive shaft 20; the guide wire tube 33 that is disposed in the vicinity of an outer surface of the outer tube 30 and has the guide wire lumen 33A formed therein; the metal member 70 at least a part of which is disposed on the distal side with respect to the cutting portion 40; and the distal tip 35 that is interlocked with the distal portion of the metal member 70, is positioned on the distal side with respect to the metal member 70, and is made of the resin, in which the distal tip 35 has the distal lumen 36 that communicates with the guide wire lumen 33A and is positioned on the distal side with respect to the guide wire lumen 33A, the metal member 70 has at least one of recesses 76 and 82 on an outer peripheral surface thereof, at least a part of inner surfaces of the recesses 76 and 82 faces the proximal side, and the distal tip 35 is inserted into the recesses 76 and 82.

In the medical device 10 configured as described above, the distal tip 35 made of a resin disposed on the distal side with respect to the metal member 70 is more flexibly deformed than the metal member 70. Therefore, in the medical device 10, the followability to the guide wire W inserted into the guide wire lumen 33A and the body lumen (for example, a blood vessel) is improved. Further, since the distal tip 35 engages with the recesses 76 and 82, peeling, separation, and the like from the metal member 70 are prevented. Therefore, the medical device 10 includes the metal member 70 on the distal side with respect to the cutting portion 40, has the high followability to the guide wire W and the blood vessel, and can prevent breakage of the distal tip 35 made of the resin.

In addition, the distal tip 35 covers the entire recesses 76 and 82. Accordingly, the distal tip 35 is firmly interlocked with the recesses 76 and 82. Therefore, it is possible to prevent the peeling and separation of the distal tip 35 from the metal member 70. Note that the distal tip 35 may partially cover the recesses 76 and 82. That is, a part of the second recesses 82 may be covered with the distal tip 35, and a part of the second recesses 82 may be exposed to the outside. In addition, a part of the first recesses 76 may be covered with the distal tip 35, and a part of the first recesses 76 may be exposed to the outside.

In addition, the recesses 76 and 82 are through holes or non-through holes. Accordingly, portion of the distal tip 35 that are in the recesses 76 and 82 is firmly interlock with the recesses 76 and 82. Therefore, it is possible to effectively prevent the peeling and the separation of the distal tip 35 from the metal member 70. When the recesses 76 and 82 penetrate, an amount of the distal tip 35 entering the recesses 76 and 82 is likely to increase, and thus the distal tip 35 is firmly interlocked with recesses 76 and 82. If the recesses 76 and 82 do not penetrate, the distal tip 35 can reliably enter the recesses 76 and 82, and it is possible to prevent occurrence of unintended gaps in the recesses 76 and 82.

In addition, the metal member 70 includes the fixing portion 71 that fixes the outer tube 30 and the guide wire tube 33, and at least one of the recesses is the first recess 76 formed on the side surface 75 of the fixing portion 71. Accordingly, the distal tip 35 is firmly interlocked with the first recess 76. Therefore, it is possible to effectively prevent the peeling and the separation of the distal tip 35 from the metal member 70.

In addition, the guide wire tube 33 is made of a material having a melting point higher than that of the distal tip 35, and the distal tip 35 covers at least a part of an outer peripheral surface of a distal side of the guide wire tube 33. Accordingly, deformation of the guide wire tube 33 due to heating at the time of forming the distal tip 35 can be prevented.

In addition, the guide wire tube 33 is made of a material that is harder than the distal tip 35 and softer than the metal member 70, the most distal end of the guide wire tube 33 is located on the proximal side with respect to the most distal end of the distal tip 35, and the most distal end of the metal member 70 is located on the proximal side with respect to the most distal end of the guide wire tube 33. Accordingly, rigidity of the medical device 10 gradually increases toward the proximal side. Therefore, the medical device 10 has an improved balance of the rigidity and the followability to the guide wire W or the blood vessel, and is less likely to be damaged. Note that hardness of the material can be specified by, for example, Rockwell hardness, Brinell hardness, Vickers hardness, Shore hardness, Durometer hardness, or the like.

In addition, the medical device 10 includes the heat-shrinkable first fixing tube 90 that surrounds the guide wire tube 33 and the metal member 70. Accordingly, the first fixing tube 90 can prevent the guide wire tube 33, through which the guide wire W is passed and which is easily bent, from moving away from the metal member 70. Therefore, the peeling and the separation of the guide wire tube 33 from the metal member 70 can be effectively prevented.

In addition, the first fixing tube 90 covers at least one of the first recesses 76 and is inserted into the first recess 76. Accordingly, the first fixing tube 90 enters the first recesses 76 and is firmly interlocked with the metal member 70. Therefore, the peeling and the separation of the guide wire tube 33 from the metal member 70 can be effectively prevented.

In addition, the metal member 70 is exposed to the outside between the proximal end of the distal tip 35 and the distal end of the cutting portion 40. Accordingly, since the entire metal member 70 is not required to be covered with another member, it is possible to reduce a diameter of the medical device 10.

In addition, the cutting portion 40 is formed in a tubular shape, the metal member 70 includes the fixing portion 71 that fixes the outer tube 30 and the guide wire tube 33, and the stopper 72 that is fixed to the fixing portion 71, and a part of the stopper 72 enters the inside of the cutting portion 40 from the distal side. Accordingly, before the cutting portion 40 penetrates a blood vessel wall, the stopper 72 contacts the blood vessel wall so that the cutting portion 40 cannot further move with respect to the blood vessel wall. Therefore, the stopper 72 can prevent the cutting portion 40 from cutting a portion of the blood vessel wall that should not be cut. Therefore, safety of the medical device 10 is improved.

In addition, at least one of the recesses 76 and 82 is formed on the stopper 72. Accordingly, the distal tip 35 is firmly interlocked with the second recess 82. Therefore, it is possible to effectively prevent the peeling and the separation of the distal tip 35 from the metal member 70.

In addition, the stopper 72 includes the inclined portion 80, the inclined portion 80 is inclined such that the distance from the fixing portion 71 increases toward the proximal side, and at least a part of the inclined portion 80 is exposed to the outside. Accordingly, the metal member 70 can be brought into contact with the body lumen by the inclined portion 80 exposed to the outside. Therefore, the medical device 10 can smoothly move in the body lumen and prevent the unintended damage to the body lumen.

Note that this disclosure is not limited to the examples described above, and various modifications can be made by those skilled in the art within a scope of the technical idea of this disclosure. For example, a body lumen into which the medical device 10 can be inserted is not limited to a blood vessel, and may be, for example, a vessel, a urinary duct, a bile duct, a fallopian tube, or a hepatic duct. Therefore, an object to be cut may not be a thrombus.

In addition, in the medical device 10, the first recess 76 may not be formed as long as the second recess 82 is formed. In addition, in the medical device 10, the second recess 82 may not be formed as long as the first recess 76 is formed.

In addition, the medical device 10 and the drive device 100 may be integrally configured to form a single medical system 1.

What is claimed is:

1. A medical device that removes an object in a body lumen, the medical device comprising:
   a rotatable drive shaft;
   a cutter attached to a distal portion of the drive shaft and by which the object is cut;
   an outer tube surrounding the drive shaft;
   a guide wire tube attached to a distal portion of the outer tube and having a guide wire lumen therein;

a metal member attached to the guide wire tube and including a first portion that extends along the guide wire tube and includes a first recess; and a distal tip made of a resin, disposed at a distal portion of the guide wire tube, and having a distal lumen that communicates with the guide wire lumen, wherein the distal tip engages with the first recess of the metal member.

2. The medical device according to claim 1, further comprising:
   a first fixing tube that attaches the metal member to the guide wire tube; and
   a second fixing tube that attaches the guide wire tube to an outer surface of the distal portion of the outer tube.

3. The medical device according to claim 1, wherein the first recess of the metal member includes a surface that is curved with respect to a direction parallel to a rotational axis of the drive shaft.

4. The medical device according to claim 1, wherein the distal tip completely covers the first recess of the metal member.

5. The medical device according to claim 1, wherein the first recess penetrates the first portion of the metal member.

6. The medical device according to claim 1, wherein the first portion of the metal member is between the guide wire tube and the outer tube on a proximal side of the cutter and is between the guide wire tube and the distal tip on a distal side of the cutter.

7. The medical device according to claim 1, wherein
   the guide wire tube is made of a material having a melting point higher than that of the distal tip, and
   the distal tip covers at least a part of an outer peripheral surface of the distal portion of the guide wire tube.

8. The medical device according to claim 1, wherein
   the guide wire tube is made of a material that is harder than the distal tip and softer than the metal member, and
   a distal end of the guide wire tube is between a distal end of the distal tip and a distal end of the metal member.

9. The medical device according to claim 1, further comprising:
   a heat-shrinkable fixing tube that attaches the metal member to the guide wire tube.

10. The medical device according to claim 9, wherein the fixing tube covers the first recess of the metal member.

11. The medical device according to claim 1, wherein the first portion of the metal member includes a first surface in contact with the guide wire tube and a second surface opposite to the first surface that is not in contact with the guide wire tube.

12. The medical device according to claim 1, wherein
   the cutter is formed in a tubular shape,
   the first portion of the metal member is between the guide wire tube and the outer tube,
   the metal member further includes a stopper portion that is fixed to the first portion and located on a distal side of the cutter, and
   a part of the stopper portion is surrounded by the cutter.

13. The medical device according to claim 12, wherein the stopper portion includes a second recess that engages with the distal tip.

14. The medical device according to claim 12, wherein
   the stopper portion includes an inclined surface that is inclined with respect to the guide wire tube, and
   a distance between the inclined surface and the guide wire tube decreases toward a distal end of the metal member.

15. The medical device according to claim 1, wherein the metal member includes a second recess at a proximal side of the first recess.

16. A medical system that removes an object in a body lumen, the medical system comprising:
   a drive device configured to generate a rotational force; and
   a medical device connectable to the drive device and including:
      a drive shaft rotatable according to the rotational force,
      a cutter attached to a distal portion of the drive shaft and by which the object is cut,
      an outer tube surrounding the drive shaft,
      a guide wire tube attached to a distal portion of the outer tube and having a guide wire lumen therein,
      a metal member attached to the guide wire tube and including a first portion that extends along the guide wire tube and includes a first recess, and
      a distal tip made of a resin, disposed at a distal portion of the guide wire tube, and having a distal lumen that communicates with the guide wire lumen, wherein the distal tip engages with the first recess of the metal member.

17. The medical system according to claim 16, wherein the medical device further includes a first housing that is rotatable and connected to a proximal portion of the outer tube.

18. The medical system according to claim 17, wherein
   the medical device further includes a second housing connectable to the drive device, and
   the first housing is rotatable with respect to the second housing.

19. The medical system according to claim 16, wherein the drive device includes an aspiration tube communicating with a lumen in the drive shaft and through which the object removed from the body lumen is aspirated.

20. A method of removing an object in a body lumen using a medical device that includes:
   a rotatable drive shaft,
   a cutter attached to a distal portion of the drive shaft and by which the object is cut,
   an outer tube surrounding the drive shaft,
   a guide wire tube attached to a distal portion of the outer tube and having a guide wire lumen therein;
   a metal member attached to the guide wire tube and including a first portion that extends along the guide wire tube and includes a first recess, and
   a distal tip made of a resin, disposed at a distal portion of the guide wire tube, and having a distal lumen that communicates with the guide wire lumen, the distal tip engaging with the first recess of the metal member, the method comprising:
   inserting a guide wire into a blood vessel to reach a lesion area;
   inserting a proximal end of the guide wire into the guide wire lumen of the guide wire tube via the distal lumen of the distal tip;
   bringing a distal portion of the medical device to the lesion area; and
   rotating the drive shaft to cut the object by the cutter.

* * * * *